United States Patent [19]

Koch

[11] 3,950,414

[45] Apr. 13, 1976

[54] PREPARATION OF AROMATIC DIACID CHLORIDES

[75] Inventor: Theodore A. Koch, Wilmington, Del.

[73] Assignee: E. I. Du Pont de Nemours and Company, Wilmington, Del.

[22] Filed: Jan. 30, 1974

[21] Appl. No.: 437,857

[52] U.S. Cl. .......................................... 260/544 D
[51] Int. Cl.² ...................................... C07C 63/22
[58] Field of Search ................................ 260/544 D

[56] References Cited
UNITED STATES PATENTS

| | | | |
|---|---|---|---|
| 1,851,832 | 3/1932 | Henderson et al. | 260/544 M |
| 1,880,169 | 9/1932 | Bennett | 260/544 M |
| 2,180,772 | 11/1939 | Scherer | 260/544 M |
| 3,274,242 | 9/1966 | Etherington et al. | 260/544 M |

*Primary Examiner*—Anton H. Sutto

[57] ABSTRACT

An aromatic dicarboxylic acid chloride, e.g., terephthaloyl chloride, is prepared by reacting chlorine with a solution of an aromatic dialdehyde in an inert solvent, e.g., carbon tetrachloride, at a temperature of about from 0°C. to 125°C. Essentially complete conversion of the aldehyde to the chloride is achieved under these conditions.

8 Claims, No Drawings

PREPARATION OF AROMATIC DIACID CHLORIDES

BACKGROUND OF THE INVENTION

1. Field of the Invention

This invention relates to an improved method of preparing aromatic dicarboxylic acid chlorides by the reaction of aromatic dialdehydes with chlorine.

2. Description of the Prior Art

Aromatic dicarboxylic acid chlorides, e.g., terephthaloyl chloride, undergo polymer-forming condensation reactions with diamines and glycols and thus are important as intermediates in the preparation of polyamides and polyesters. One of the methods known to the art for preparing such acid chlorides involves the reaction of aromatic aldehydes with chlorine. In this method, which is described in U.S. Pat. No. 3,274,242, the chlorination is conducted in the vapor phase at elevated temperatures, e.g., in the range of about from 350°C. to 450°C. for terephthalaldehyde chlorination. The presence of the dialdehyde in the vapor phase together with the use of high temperatures heretofore has been indicated to be critical to obtaining a high yield of the dichloride in this reaction. Also, large excesses of chlorine have been indicated to be beneficial. However, despite such relatively severe conditions, the use of which is associated with economic and technical disadvantages, the vaporphase chlorination method has been shown to give only a relatively low degree of conversion of the aldehyde to the chloride, i.e., less than 40 percent.

The art also describes the chlorination of certain liquid aldehydes, i.e., aromatic monoaldehydes, at temperatures of 125°C. to 160°C. (Gilman, *Organic Syntheses*, Coll. Vol. 1, Ed. 2, 1941, p. 155), but the reaction has been shown to be discouragingly slow, i.e., on the order of 15–30 hours of o-chlorobenzaldehyde chlorination.

SUMMARY OF THE INVENTION

The present invention provides an improved process for preparing aromatic dicarboxylic acid chlorides, e.g., terephthaloyl chloride, which comprises contacting a solution of an aromatic dialdehyde, e.g., terephthalaldehyde, in an inert solvent with chlorine at a temperature in the range of about from 0°C. to 125°C., preferably up to about 75°C.

The process preferably is carried out with an amount of chlorine which is slightly, e.g., up to about 10 percent, in excess of stoichiometric, and with a fully halogenated hydrocarbon solvent, e.g., carbon tetrachloride.

Surprisingly it has been found that the degree of conversion of aromatic dialdehydes to diacid chlorides is about 3 times higher when chlorine is contacted with a solution of the aldehyde at relatively low temperatures, i.e., about from 0°C. to 125°C., despite the use of smaller chlorine/aldehyde molar ratios, as contrasted to contacting the chlorine with aldehyde vapor at considerably higher temperatures as described in the art. Thus, the present process affords improved results in terms of product yield while affording the advantages accruing from the use of less severe operating conditions. Furthermore, the present process is effected within reasonable reaction times, e.g., less than an hour, as contrasted to the liquid monoaldehyde chlorination reaction described in the art.

DETAILED DESCRIPTION

In the present process, the dialdehyde is chlorinated in the liquid phase, i.e., in solution in a solvent which is inert with respect to the aldehyde and chlorine under the reaction conditions employed. While solvents for the dialdehyde and chlorine which undergo light-induced chlorination, e.g., aromatic hydrocarbons such as toluene and xylene, can be used provided light is excluded from the reaction mixture, solvents which undergo little or no reaction with chlorine when exposed to light are preferred as their use requires no special measures to exclude light. On this basis, the preferred solvents include halogenated aliphatic and aromatic hydrocarbons, e.g., carbon tetrachloride, chloroform, and chlorobenzene, the fully halogenated compounds being especially preferred on the basis of their complete inertness. Benzene can be inert under certain circumstances and therefore also can be used as a solvent.

The dialdehyde solution is contacted with chlorine at a temperature ranging from about 0°C. to a moderately elevated temperature, i.e., up to about 125°C., and preferably from about 20°C. to about 75°C., the specific temperature employed being below the boiling point of the solvent at the prevailing pressure. At temperatures below about 125°C. the likelihood of the occurrence of side-reactions and the formation of by-products is minimized, and corrosion problems also are less likely to arise. Also, a drop in the solubility of the chlorine in the solvent, although possible to overcome by the application of pressure, is avoided.

The present process affords a high degree of conversion without the need for substantial excesses of chlorine. The stoichiometric amount of chlorine required to chlorinate both aldehyde groups, i.e., a 2/1 chlorine/dialdehyde molar ratio, is sufficient, although it is preferred to use an amount in slight excess of stoichiometric, e.g., up to about 10 percent excess (up to 2.2/1 molar ratio), to assure that the required stoichiometric amount is maintained.

Although superatmospheric pressure can be employed in the present process, it is not believed to have any notable effect on the course of the reaction, and accordingly is not preferred except in cases in which, for example, the boiling point of the solvent at atmospheric pressure is too low, the degree of solubility of chlorine in the solvent at the reaction temperature used is too low, etc.

The reaction can be performed as a batch operation or continuously. Higher reaction rates may be achieved in a continuous operation in which the dichloride product is present in the mixture in which the chlorination takes place.

Dicarboxylic acid chlorides which can be prepared by the present process include terephthaloyl and isophthaloyl chlorides (from terephthal- and isophthalaldehyde, respectively); chlorides of binuclear dicarboxylic acids, e.g., bibenzoic acid (from biphenyldicarboxaldehydes); and condensed-ring acid chlorides, e.g., naphthalenedicarboxylic acid chlorides (from naphthalenedicarboxaldehydes).

The following example is illustrative of specific embodiments of the process of the invention.

EXAMPLE

Five grams of terephthalaldehyde (0.037 mole) and 200 milliliters of carbon tetrachloride are charged to a one-liter round-bottomed flask equipped with a central paddle stirrer, a gas inlet arm, and a reflux condenser. At 35°C., chlorine is introduced into the flask at atmospheric pressure at a rate such that a slightly yellowish color of the carbon tetrachloride solution is maintained. 0.0775 mole of chlorine is introduced over a period of 0.5 hour. Gas chromatographic analysis of a sample of the reaction mixture withdrawn thereafter shows only terephthaloyl chloride. Infrared analysis of the solid product remaining after evaporation of the carbon tetrachloride shows only terephthaloyl chloride.

Similar results are obtained when the above procedure is repeated with the exception that isophthalaldehyde is substituted for terephthalaldehyde.

I claim:

1. In a process for producing aromatic dicarboxylic acid chlorides by the reaction of aromatic dialdehydes with chlorine, the improvement which comprises contacting the aromatic dialdehyde in the liquid phase with chlorine at a temperature in the range of about from 0° to 125°C., said dialdehyde being one in which the aldehyde groups are attached directly to an aromatic nucleus and being dissolved in a solvent which is inert with respect to said dialdehyde and to chlorine under the reaction conditions employed, said solvent being selected from the group consisting of aromatic hydrocarbons and halogenated hydrocarbons.

2. A process of claim 1 wherein said solvent is a chlorinated hydrocarbon.

3. A process of claim 2 wherein said chlorinated hydrocarbon is carbon tetrachloride.

4. A process of claim 1 wherein said dialdehyde is selected from the group consisting of terephthalaldehyde, isophthalaldehyde, biphenyldicarboxaldehydes, and naphthalenedicarboxaldehydes.

5. A process of claim 4 wherein said dialdehyde is terephthalaldehyde.

6. A process of claim 1 wherein said solvent is a fully halogenated aliphatic hydrocarbon.

7. In a process for producing terephthaloyl chloride by the reaction of terephthalaldehyde with chlorine, the improvement which comprises contacting terephthalaldehyde in the liquid phase with chlorine at a temperature in the range of about from 20°C. to 75°C., the molar ratio of chlorine to terephthalaldehyde being about from 2/1 to 2.2/1, said terephthalaldehyde being dissolved in a solvent which is inert with respect thereto and with respect to chlorine under the reaction conditions employed.

8. A process of claim 7 wherein said terephthalaldehyde is dissolved in a solvent selected from the group consisting of aromatic hydrocarbons and halogenated hydrocarbons.

* * * * *